(12) United States Patent
Gray et al.

(10) Patent No.: US 7,803,979 B2
(45) Date of Patent: Sep. 28, 2010

(54) METHOD FOR REMOVING WATER FROM AN ALKYLATION PROCESS SYSTEM

(75) Inventors: Robert M. Gray, Sapulpa, OK (US); Keith W. Hovis, Stillwater, OK (US)

(73) Assignee: UOP LLC, Des Plaines, IL (US)

( * ) Notice: Subject to any disclaimer, the term of this patent is extended or adjusted under 35 U.S.C. 154(b) by 781 days.

(21) Appl. No.: 11/712,110

(22) Filed: Feb. 28, 2007

(65) Prior Publication Data

US 2008/0207976 A1 Aug. 28, 2008

(51) Int. Cl.
*C07C 7/05* (2006.01)
(52) U.S. Cl. .................. 585/704; 585/712; 585/723; 585/724; 585/730; 585/802; 502/35; 502/36
(58) Field of Classification Search ............ 502/35, 502/36; 585/712, 723, 724, 730, 802, 704
See application file for complete search history.

(56) References Cited

U.S. PATENT DOCUMENTS

| 3,007,982 A | * | 11/1961 | Clauson ................. 585/715 |
| 5,382,746 A | | 1/1995 | Child et al. ............. 585/802 |
| 5,386,076 A | | 1/1995 | Child et al. ............. 585/802 |
| 5,461,183 A | | 10/1995 | Del Rossi et al. ........ 585/802 |
| 5,759,937 A | | 6/1998 | Hovis et al. ............. 502/36 |
| 5,767,335 A | | 6/1998 | Anderson et al. ........ 585/723 |
| 2003/0130553 A1 | * | 7/2003 | Randolph et al. ........ 585/723 |

FOREIGN PATENT DOCUMENTS

WO    WO 99/31485 A1    6/1999

* cited by examiner

*Primary Examiner*—Glenn Caldarola
*Assistant Examiner*—Prem C. Singh
(74) *Attorney, Agent, or Firm*—James C Paschall

(57) ABSTRACT

A method is disclosed for removing water from an alkylation process system using a water removal column to remove water from a re-run column (catalyst regeneration column) overhead stream.

17 Claims, No Drawings

METHOD FOR REMOVING WATER FROM AN ALKYLATION PROCESS SYSTEM

The present invention relates to the alkylation of olefinic hydrocarbons with isoparaffin hydrocarbons in the presence of an alkylation catalyst mixture comprising hydrofluoric acid (HF) and, optionally, a volatility reducing additive. More particularly, the invention relates to the removal of water from an alkylation process system by use of a water removal column.

BACKGROUND OF THE INVENTION

The use of catalytic alkylation processes to produce branched hydrocarbons having properties that are suitable for use as gasoline blending components is well known in the art. Generally, the alkylation of olefins by saturated hydrocarbons, such as isoparaffins, is accomplished by contacting the reactants with an acid catalyst to form a reaction mixture, settling the mixture to separate the catalyst from the hydrocarbons and further separating the alkylation reactor effluent, for example, by fractionation, to recover the separate product streams. Normally, the alkylation reactor effluent of the alkylation process contains hydrocarbons having five to sixteen carbon atoms per molecule, preferably seven to nine carbon atoms per molecule. In order to have the highest quality gasoline blending stock, it is preferred for the alkylate hydrocarbons formed in the alkylation process to be highly branched and contain seven to nine carbon atoms per molecule.

Recent efforts to improve conventional hydrogen fluoride catalyzed alkylation processes have resulted in the development of new catalyst compositions that contain hydrogen fluoride and a volatility reducing additive. These new catalyst compositions have been found to be quite effective as alkylation catalysts and provide many other favorable benefits.

Regeneration of an alkylation catalyst mixture containing water, HF, acid soluble oil (ASO), and, optionally, a volatility reducing additive generally includes stripping HF from the catalyst mixture using a combination of elevated temperature and isoparaffin or paraffin stripping gas, for inclusion of the stripped HF with the alkylation catalyst mixture. The overhead stream also contains water. The bottoms stream from such a stripper (commonly referred to as a re-run column) contains the ASO and, if present, the volatility reducing additive. Where a volatility reducing additive is used, the re-run column bottoms stream is then separated into an ASO stream and a volatility reducing additive stream, and the volatility reducing additive stream is combined with the alkylation catalyst. Water which enters the unit with the hydrocarbon feed must be removed. Elevated levels of water in the alkylation catalyst can result in increased corrosion of process equipment and alkylate quality degradation. Removal of this water is currently done either by adjusting operation of the stripper to force the water and HF out the bottom with the ASO or if the volatility additive is present, removing a vapor product from the side of the stripping column. Both options involve loss of significant quantities of HF. Therefore, development of an efficient process for removing water from the alkylation process system would be a significant contribution to the art.

DETAILED DESCRIPTION OF THE INVENTION

In accordance with the present invention, an olefin can be alkylated with a first isoparaffin in the presence of an alkylation catalyst mixture comprising, consisting of, or consisting essentially of HF and water in an alkylation reactor to thereby produce an alkylation reaction effluent comprising, consisting of, or consisting essentially of an alkylate product, an ASO reaction by-product, and the alkylation catalyst mixture.

In another embodiment, the alkylation catalyst mixture comprises, consists of, or consists essentially of HF, water and a volatility reducing additive.

The olefin can be any olefin suitable for alkylation. Preferably, the olefin comprises, consists of, or consists essentially of at least one olefinic hydrocarbon having at least 3 carbon atoms per molecule and, more preferably, 3 to 4 carbon atoms per molecule. The first isoparaffin preferably comprises, consists of, or consists essentially of at least one isoparaffinic hydrocarbon having at least 4 carbon atoms per molecule, and, more preferably, 4 to 5 carbon atoms per molecule. Most preferably, the olefin is selected from the group consisting of propylene, butene-1, isobutene, 2-butenes, methyl butenes, pentenes and combinations of any two or more thereof; and the first isoparaffin is selected from the group consisting of isobutane, isopentane, and combinations thereof.

The volatility reducing additive can be any compound effective in reducing the volatility of a mixture resulting from the addition of the volatility reducing additive to hydrofluoric acid. More particularly, the volatility reducing additive can be a compound selected from the group consisting of sulfone, ammonia, methylamines, ethylamines, propylamines, butylamines, pentylamines, pyridine, alkylpyridines, melamine, hexamethylene-tetramine and the like, and combinations of any two or more thereof.

The sulfones suitable for use in this invention are the sulfones of the general formula

wherein R and $R^1$ are monovalent hydrocarbon alkyl or aryl substituents, each containing from 1 to 8 carbon atoms, and wherein R and $R^1$ can be the same or different. Examples of suitable sulfones include, but are not limited to, dimethylsulfone, di-n-propylsulfone, diphenylsulfone, ethylmethylsulfone and alicyclic sulfones wherein the $SO_2$ group is bonded to a hydrocarbon ring. In such a case, R and $R^1$ are forming together a branched or unbranched hydrocarbon divalent moiety preferably containing from 3 to 12 carbon atoms. Among the latter, tetramethylenesulfone or sulfolane, 3-methylsulfolane and 2,4-dimethylsulfolane are more particularly suitable since they offer the advantage of being liquid at process operating conditions of concern herein. These sulfones may also have substituents, particularly one or more halogen atoms, such as for example, chloromethylethylsulfone. These sulfones may advantageously be used in the form of mixtures of any two or more thereof. The most preferred volatility reducing additive is sulfolane.

As used within this description and in the appended claims, the term "acid soluble oil", or "ASO", means those conjunct polymers which are highly olefinic oils produced by acid-catalyzed reactions of hydrocarbons. An extensive description and characterization of certain types of conjunct polymer oils is provided in the *Journal of Chemical and Engineering Data* article entitled "Molecular Structure of conjunct Polymers", pages 150-160, Volume 8, Number 1, (January 1963) by Miron and Lee. This article is incorporated herein by reference.

The physical properties of ASO depend upon the particular hydrocarbon feed processed, the catalyst utilized in the process, feed contaminants such as hydrogen sulfide, butadiene, oxygenates and other compounds, and the alkylation process reaction conditions.

The alkylation reaction effluent can be passed from the alkylation reactor to a separator wherein a phase separation occurs. The phase separation produces a hydrocarbon phase. The hydrocarbon phase can comprise, consist of, or consist essentially of the alkylate product and unreacted isoparaffins and can be removed from the separator for further downstream processing.

The phase separation in the separator also produces an alkylation catalyst mixture phase which can be used, at least in part, as the alkylation catalyst mixture. The alkylation catalyst mixture phase comprises, consists of, or consists essentially of the alkylation catalyst mixture and at least a portion of the ASO reaction by-product produced.

To regenerate the alkylation catalyst mixture, at least a portion of the alkylation catalyst mixture phase (which can also be referred to as a slip stream) is passed to a re-run column, which provides means for separating the alkylation catalyst mixture phase into a re-run column bottoms stream and a re-run column overhead stream. The remaining portion of the alkylation catalyst mixture phase is recycled to the alkylation reaction zone for use as the alkylation catalyst mixture. The slip stream of the alkylation catalyst mixture phase is contacted, within the re-run column, with an upwardly flowing gas stream comprising a hydrocarbon selected from the group consisting of a second isoparaffin, a paraffin, and combinations thereof, to provide the re-run column bottoms stream comprising, consisting of, or consisting essentially of at least a portion of the ASO reaction by-product and, where a volatility reducing additive is present in the alkylation catalyst mixture, the re-run column bottoms stream comprises, consists of, or consists essentially of at least a portion of the ASO reaction by-product and at least a portion of the volatility reducing additive. Also provided is the re-run column overhead stream comprising, consisting of, or consisting essentially of HF, at least a portion of the gas stream, and water.

A portion of the first isoparaffin can be used as the second isoparaffin.

The second isoparaffin preferably comprises, consists of, or consists essentially of at least one isoparaffinic hydrocarbon having at least 4 carbon atoms per molecule, and, more preferably, 4 to 5 carbon atoms per molecule. Most preferably, the second isoparaffin is selected from the group consisting of isobutane, isopentane, and combinations thereof. The paraffin preferably comprises, consists of, or consists essentially of at least one paraffinic hydrocarbon having 3 or 4 carbon atoms per molecule.

At least a portion of the re-run column overhead stream can be added to the remaining portion of the alkylation catalyst mixture phase recycled to the alkylation reactor prior to alkylating the olefin with the first isoparaffin, or, added to the alkylation catalyst mixture phase in the separator, in either case for eventual use as part of the alkylation catalyst mixture.

The re-run column bottoms stream can be passed downstream for further processing.

Optionally, a re-run column side draw stream can be removed from the re-run column at a location between the locations for removal of the re-run column bottoms stream and the re-run column overhead stream. The re-run column side draw stream comprises a portion of said gas stream, HF, water and contaminants selected from the group consisting of amides, oxygenates, sulfides and aromatics. Such contaminants either come in with the feed or are produced in the alkylation process system. The re-run column side draw stream can be passed to a condenser from which isoparaffins or paraffins can be recycled for use in the alkylation process system, and which produces a condensed acid phase which typically contains greater than 60 wt. % HF.

A portion of the re-run column overhead stream is used as a bottoms feed to the bottom section of a water removal column which also comprises, consists of, or consists essentially of a bottom section, an intermediate section and a top section.

The bottom section and intermediate section can each contain a mass transfer medium for mass transfer between liquids and vapors. The mass transfer medium is selected from the group consisting of distillation trays, distillation packing, and combinations thereof.

The top section has a top section temperature and can contain a condenser for condensing water out of any material entering into the top section. The condenser can comprise at least one conduit through which cooling water is passed.

A stripping stream comprising, consisting of, or consisting essentially of the vaporous portion of the bottoms feed is allowed to upwardly flow to the intermediate section and the top section.

Water is condensed out of the material entering into the top section forming a condensed stream comprising, consisting of, or consisting essentially of water. The amount of water condensed out of the material entering the top section can be controlled by a procedure selected from the group consisting of: 1) adjusting the flow rate of the cooling water; 2) adjusting the temperature of the cooling water; and 3) combinations thereof.

The condensed stream is then allowed to flow downwardly from the top section to the intermediate section and the bottom section for contact with the upwardly flowing stripping stream to thereby strip HF and hydrocarbons from the condensed stream into the stripping stream; and to condense and transfer water contained in the stripping stream to the condensed stream.

A water removal column overhead stream, having a water removal column overhead stream temperature and which comprises, consists of, or consists essentially of hydrocarbons and HF, is removed from the top section and passed to the separator. A water removal column bottom effluent comprising, consisting of, or consisting essentially of water is removed from the bottom section. The water removal column bottom effluent can also comprise, consist of, or consist essentially of water and HF, and have a mass ratio of HF to water less than about 7, more preferably less than about 6, and most preferably less than about 5.

Optionally, a portion of the re-run column overhead stream can be charged to the water removal column at a location just below the intermediate section as an intermediate section feed which has an intermediate section feed temperature. The vaporous portion of the intermediate section feed joins with and becomes a part of the stripping stream which is upwardly flowing to the intermediate section and the top section.

The amount of water removed from the alkylation process system in the water removal column bottom effluent can be controlled by a procedure selected from the group consisting of: 1) altering the top section temperature (controlling the amount of water condensing in the top section); 2) altering the flow rate of the bottoms feed; 3) altering the flow rate of the intermediate section feed; and 4) combinations thereof.

A target overhead temperature for the water column overhead stream can be established based on the desired level of water removal. The top section temperature can be adjusted in response to the intermediate section feed temperature and the water column overhead stream temperature in order to move the water column overhead stream temperature toward the target overhead temperature.

Alternately, a target differential temperature between the water column overhead stream temperature and the intermediate section feed temperature can be established based on the desired level of water removal. The top section temperature can be adjusted in response to the intermediate section feed temperature and the water column overhead stream temperature in order to move the differential temperature between the water column overhead stream temperature and the intermediate section feed temperature toward the target differential temperature.

Example

The following computer model examples demonstrate the advantages of the present invention. These examples are for illustration purposes only and they are not intended to limit the invention as set out in the specification and the appended claims.

The following processes were modeled using a computer modeling program.

Control Model

In this Control Model, an acid catalyst feed and a stripping gas feed, having the compositions and mass flows as shown in Table 1, were fed to a re-run column. A re-run column bottoms stream, a re-run column overhead stream, and a re-run column side draw stream were removed from the re-run column. The weight percent of water removal (based on the amount of water entering the re-run column), and mass ratio of HF to water, for the re-run column side draw stream are shown in Table 2.

Inventive Process—Model 1

In this Model 1, the re-run column overhead stream from the Control Model was sent to a water removal column from which a water removal column overhead stream and a water removal column bottom effluent were removed. The mass ratio of the water removal column bottom effluent to the water removal column overhead stream for this Model 1 was set at 0.005. The weight percent of water removal (based on the amount of water entering the re-run column), and mass ratio of HF to water, for the water removal column bottom effluent are shown in Table 2.

Inventive Process—Model 2

In this Model 2, the re-run column overhead stream from the Control Model was sent to a water removal column from which a water removal column overhead stream and a water removal column bottom effluent were removed. The mass ratio of the water removal column bottom effluent to the water removal column overhead stream for this Model 2 was set at 0.010. The weight percent of water removal (based on the amount of water entering the re-run column), and mass ratio of HF to water, for the water removal column bottom effluent are shown in Table 2.

TABLE 1

| Mass Fraction | Acid Catalyst Feed | Stripping Gas Feed | Combined Feed |
| --- | --- | --- | --- |
| Propane | 0.00 | 0.02 | 0.01 |
| Isobutane | 0.05 | 0.82 | 0.41 |
| n-butane | 0.01 | 0.16 | 0.08 |
| HF | 0.78 | 0.00 | 0.41 |

TABLE 1-continued

| Mass Fraction | Acid Catalyst Feed | Stripping Gas Feed | Combined Feed |
| --- | --- | --- | --- |
| Water | 0.02 | 0.00 | 0.01 |
| Additive | 0.10 | 0.00 | 0.05 |
| ASO | 0.04 | 0.00 | 0.02 |
| Total | 1.00 | 1.00 | 1.00 |
| Mass Flow lb/hr | 37,903 | 33,920 | 71,823 |

TABLE 2

| Model | Re-run Column Side Draw Stream | | Water Removal Column Bottom Effluent | | Overall (combined) | |
| --- | --- | --- | --- | --- | --- | --- |
| | Wt. % Water Removal* | HF/water Mass Ratio | Wt. % Water Removal* | HF/water Mass Ratio | Wt. % Water Removal* | HF/water Mass Ratio |
| Control Model | 0.9 | 6.4 | N/A | N/A | 0.9 | 6.4 |
| Inventive Model 1 | 0.9 | 6.4 | 11.3 | 2.8 | 12.2 | 3.1 |
| Inventive Model 2 | 0.9 | 6.4 | 17.1 | 4.0 | 18.0 | 4.1 |

$$* = \frac{\text{weight of water removed by this stream or combination of streams}}{\text{Combined weight of water fed to the re-run column in the acid catalyst and stripping gas feeds}} \times 100$$

As can be seen from the calculated data in Table 2, the inventive process results in a much higher water removal weight percentage, 12.2% and 18% for Models 1 and 2, respectively, as compared to the control process which was 0.9% for the Control Model. Also, the overall mass ratio of HF to water in the water removal streams is much lower for the inventive process, 3.1 and 4.1 for Models 1 and 2, respectively, as compared to the control process which was 6.4 for the Control Model.

Reasonable variations, modifications, and adaptations can be made within the scope of the disclosure and the appended claims without departing from the scope of this invention.

That which is claimed is:

1. A method for removing water from an alkylation process system, said method comprising the steps of:
    alkylating an olefin with a first isoparaffin in the presence of an alkylation catalyst mixture comprising HF and water in an alkylation reactor thereby producing an alkylate product and an ASO reaction by-product;
    passing an alkylation reaction effluent comprising said alkylate product, said ASO reaction by-product and said alkylation catalyst mixture from said alkylation reactor to a separator for separating said alkylation reaction effluent into a hydrocarbon phase comprising said alkylate product, and an alkylation catalyst mixture phase comprising said alkylation catalyst mixture and at least a portion of said ASO reaction by-product;
    passing at least a portion of said alkylation catalyst mixture phase to a re-run column for contact with an upwardly flowing gas stream comprising a hydrocarbon selected from the group consisting of a second isoparaffin, a paraffin, and combinations thereof, to provide a re-run column bottoms stream comprising at least a portion of said ASO reaction by-product, and a re-run column overhead stream comprising HF, at least a portion of said gas stream and water;

passing a portion of said re-run column overhead stream to said separator;

providing a water removal column comprising a bottom section, an intermediate section, and a top section;

using a portion of said re-run column overhead stream as a bottoms feed to said bottom section of said water removal column;

upwardly flowing a stripping stream comprising the vaporous portion of said bottoms feed up to said intermediate section and said top section;

condensing water out of the material entering into said top section to form a condensed stream comprising water;

downwardly flowing said condensed stream from said top section to said intermediate section and said bottom section;

contacting said upwardly flowing stripping stream with said downwardly flowing condensed stream in said intermediate section and said bottom section to thereby strip HF and hydrocarbons from said condensed stream into said stripping stream; and to thereby condense and transfer water contained in said stripping stream to said condensed stream;

passing a water removal column overhead stream comprising hydrocarbons and HF from said top section to said separator;

removing a water removal column bottom effluent comprising water from said bottom section.

2. A method in accordance with claim 1 wherein a re-run column side draw stream is removed from said re-run column at a location between the locations for removal of said re-run column bottoms stream and said re-run column overhead stream; and wherein said re-run column side draw stream comprises a portion of said gas stream, HF, water and contaminants selected from the group consisting of amides, oxygenates, sulfides and aromatics.

3. A method in accordance with claim 1 wherein said water removal column bottom effluent comprises water and HF, and wherein the mass ratio of HF to water in said water removal column bottom effluent is less than about 7.

4. A method in accordance with claim 3 wherein said mass ratio of HF to water in said water removal column bottom effluent is less than about 6.

5. A method in accordance with claim 3 wherein said mass ratio of HF to water in said water removal column bottom effluent is less than about 5.

6. A method in accordance with claim 1 wherein a portion of said re-run column overhead stream is charged to said water removal column at a location just below said intermediate section as an intermediate section feed.

7. A method in accordance with claim 6 wherein the vaporous portion of said intermediate section feed joins with and becomes a part of said stripping stream upwardly flowing to said intermediate section and said top section.

8. A method in accordance with claim 6 wherein said top section has a top section temperature, and wherein the amount of water removed from said alkylation process system in said water removal column bottom effluent is controlled by a procedure selected from the group consisting of: 1) altering said top section temperature; 2) altering the flow rate of said bottoms feed; 3) altering the flow rate of said intermediate section feed; and 4) combinations thereof.

9. A method in accordance with claim 8 wherein said intermediate section feed has an intermediate section feed temperature, said water removal column overhead stream has a water removal column overhead stream temperature, wherein a target overhead temperature for said water column overhead stream is established; and wherein said top section temperature is adjusted in response to said intermediate section feed temperature and said water column overhead stream temperature in order to move said water column overhead stream temperature toward said target overhead temperature.

10. A method in accordance with claim 8 wherein said intermediate section feed has an intermediate section feed temperature; wherein said water removal column overhead stream has a water removal column overhead stream temperature; wherein a target differential temperature between said water column overhead stream temperature and said intermediate section feed temperature is established; and wherein said top section temperature is adjusted in response to said intermediate section feed temperature and said water column overhead stream temperature in order to move the differential temperature between the water column overhead stream temperature and the intermediate section feed temperature toward said target differential temperature.

11. A method in accordance with claim 1 wherein said alkylation catalyst mixture further comprises a volatility reducing additive; and wherein said alkylation catalyst mixture phase and said re-run column bottoms stream each further comprise at least a portion of said volatility reducing additive.

12. A method in accordance with claim 11 wherein said volatility reducing additive is a sulfone.

13. A method in accordance with claim 1 wherein said intermediate section and said bottom section each contain a mass transfer medium for contacting said condensed liquid with said stripping stream.

14. A method in accordance with claim 13 wherein said mass transfer medium is selected from the group consisting of distillation trays, distillation packing, and combinations thereof.

15. A method in accordance with claim 1 wherein said top section contains a condenser for condensing water out of said material entering into said top section and forming said condensed liquid.

16. A method in accordance with claim 15 wherein said condenser comprises at least one conduit through which cooling water is passed.

17. A method in accordance with claim 16 wherein the amount of water condensed out of said material entering said top section is controlled by a procedure selected from the group consisting of: 1) adjusting the flow rate of said cooling water; 2) adjusting the temperature of said cooling water; and 3) combinations thereof.

* * * * *